United States Patent
Sobering et al.

(10) Patent No.: US 8,913,716 B2
(45) Date of Patent: Dec. 16, 2014

(54) SYSTEM AND METHOD OF CALCULATING DOSE UNCERTAINTY

(71) Applicant: TomoTherapy Incorporated, Madison, WI (US)

(72) Inventors: Geoff Sobering, Madison, WI (US); Eric Schnarr, McFarland, WI (US); Kenneth J. Ruchala, Madison, WI (US)

(73) Assignee: TomoTherapy Incorporated, Madison, WI (US)

( * ) Notice: Subject to any disclaimer, the term of this patent is extended or adjusted under 35 U.S.C. 154(b) by 161 days.

(21) Appl. No.: 13/739,590

(22) Filed: Jan. 11, 2013

(65) Prior Publication Data

US 2013/0121469 A1 May 16, 2013

Related U.S. Application Data

(62) Division of application No. 12/550,184, filed on Aug. 28, 2009, now Pat. No. 8,363,784.

(60) Provisional application No. 61/092,523, filed on Aug. 28, 2008.

(51) Int. Cl.
 *A61N 5/10* (2006.01)
 *G06F 19/00* (2011.01)

(52) U.S. Cl.
 CPC .......... *A61N 5/1031* (2013.01); *G06F 19/3406* (2013.01); *G06F 19/321* (2013.01); *G06F 19/3481* (2013.01)
 USPC .............................................. 378/65; 378/64

(58) Field of Classification Search
 USPC ..................................................... 378/64–65
 See application file for complete search history.

(56) References Cited

U.S. PATENT DOCUMENTS

| | | | |
|---|---|---|---|
| 4,149,081 | A | 4/1979 | Seppi |
| 4,455,609 | A | 6/1984 | Inamura et al. |
| 4,998,268 | A | 3/1991 | Winter |
| 5,008,907 | A | 4/1991 | Norman et al. |
| 5,027,818 | A | 7/1991 | Bova et al. |
| 5,044,354 | A | 9/1991 | Goldhorn et al. |
| 5,065,315 | A | 11/1991 | Garcia |

(Continued)

FOREIGN PATENT DOCUMENTS

| | | |
|---|---|---|
| CA | 2091275 | 9/1993 |
| JP | 6007464 | 1/1994 |

(Continued)

OTHER PUBLICATIONS

Purdy, James, "3D Treatment Planning and Intensity-Modulated Radiation Therapy," Oncology, vol. 13, No. 10, suppl. 5 (Oct. 1999).

(Continued)

*Primary Examiner* — Hoon Song
(74) *Attorney, Agent, or Firm* — Michael Best & Friedrich LLP

(57) ABSTRACT

A dose calculation tool operable to generate a variance map that represents a dose uncertainty. The variance map illustrates on a point-by-point basis where high uncertainty in the dose may exist and where low uncertainty in the dose may exist. The dose uncertainty is a result of an error in one or more data parameters related to a delivery parameter or a computational parameter.

15 Claims, 8 Drawing Sheets

(56) References Cited

U.S. PATENT DOCUMENTS

| | | |
|---|---|---|
| 5,117,829 A | 6/1992 | Miller et al. |
| 5,317,616 A | 5/1994 | Swerdloff et al. |
| 5,332,908 A | 7/1994 | Weidlich |
| 5,335,255 A | 8/1994 | Seppi et al. |
| 5,351,280 A | 9/1994 | Swerdloff et al. |
| 5,391,139 A | 2/1995 | Edmundson |
| 5,394,452 A | 2/1995 | Swerdloff et al. |
| 5,405,309 A | 4/1995 | Carden, Jr. |
| 5,442,675 A | 8/1995 | Swerdloff et al. |
| 5,446,548 A | 8/1995 | Gerig et al. |
| 5,471,516 A | 11/1995 | Nunan |
| 5,511,549 A | 4/1996 | Legg et al. |
| 5,528,650 A | 6/1996 | Swerdloff et al. |
| 5,548,627 A | 8/1996 | Swerdloff et al. |
| 5,552,605 A | 9/1996 | Arata |
| 5,579,358 A | 11/1996 | Lin |
| 5,596,619 A | 1/1997 | Carol |
| 5,596,653 A | 1/1997 | Kurokawa |
| 5,621,779 A | 4/1997 | Hughes et al. |
| 5,622,187 A | 4/1997 | Carol |
| 5,625,663 A | 4/1997 | Swerdloff et al. |
| 5,647,663 A | 7/1997 | Holmes |
| 5,651,043 A | 7/1997 | Tsuyuki et al. |
| 5,661,773 A | 8/1997 | Swerdloff et al. |
| 5,668,371 A | 9/1997 | Deasy et al. |
| 5,673,300 A | 9/1997 | Reckwerdt et al. |
| 5,692,507 A | 12/1997 | Seppi et al. |
| 5,712,482 A | 1/1998 | Gaiser et al. |
| 5,724,400 A | 3/1998 | Swerdloff et al. |
| 5,751,781 A | 5/1998 | Brown et al. |
| 5,754,622 A | 5/1998 | Hughes |
| 5,754,623 A | 5/1998 | Seki |
| 5,760,395 A | 6/1998 | Johnstone |
| 5,802,136 A | 9/1998 | Carol |
| 5,818,902 A | 10/1998 | Yu |
| 5,823,192 A | 10/1998 | Kalend et al. |
| 5,835,562 A | 11/1998 | Ramsdell et al. |
| 5,870,697 A | 2/1999 | Chandler et al. |
| 5,986,274 A | 11/1999 | Akiyama et al. |
| 6,038,283 A | 3/2000 | Carol et al. |
| 6,222,905 B1 | 4/2001 | Yoda et al. |
| 6,241,670 B1 | 6/2001 | Nambu |
| 6,301,329 B1 | 10/2001 | Surridge |
| 6,345,114 B1 | 2/2002 | Mackie et al. |
| 6,385,288 B1 | 5/2002 | Kanematsu |
| 6,393,096 B1 | 5/2002 | Carol et al. |
| 6,438,202 B1 | 8/2002 | Olivera et al. |
| 6,473,490 B1 | 10/2002 | Siochi |
| 6,477,229 B1 | 11/2002 | Grosser |
| 6,535,837 B1 | 3/2003 | Schach Von Wittenau |
| 6,636,622 B2 | 10/2003 | Mackie et al. |
| 6,661,870 B2 | 12/2003 | Kapatoes et al. |
| 6,697,452 B2 | 2/2004 | Xing |
| 6,714,620 B2 | 3/2004 | Caflisch et al. |
| 6,741,674 B2 | 5/2004 | Lee |
| 6,757,355 B1 | 6/2004 | Siochi |
| 6,792,073 B2 | 9/2004 | Deasy et al. |
| 6,792,074 B2 | 9/2004 | Erbel et al. |
| 6,853,702 B2 | 2/2005 | Renner |
| 6,873,123 B2 | 3/2005 | Marchand et al. |
| 6,882,702 B2 | 4/2005 | Luo |
| 6,891,178 B2 | 5/2005 | Xing |
| 6,907,282 B2 | 6/2005 | Siochi |
| 6,984,835 B2 | 1/2006 | Harada |
| 7,015,490 B2 | 3/2006 | Wang et al. |
| 7,046,762 B2 | 5/2006 | Lee |
| 7,142,635 B2 | 11/2006 | Kamath et al. |
| 7,257,196 B2 | 8/2007 | Brown et al. |
| 7,367,955 B2 | 5/2008 | Zhang et al. |
| 7,369,645 B2 | 5/2008 | Lane |
| 7,391,026 B2 | 6/2008 | Trinkaus et al. |
| 7,400,755 B2 | 7/2008 | West et al. |
| 7,450,687 B2 | 11/2008 | Yeo et al. |
| 7,492,858 B2 | 2/2009 | Partain et al. |
| 7,496,173 B2 | 2/2009 | Goldman et al. |
| 7,505,559 B2 | 3/2009 | Kuduvalli |
| 7,519,150 B2 | 4/2009 | Romesberg et al. |
| 7,590,440 B2 | 9/2009 | Lu et al. |
| 7,620,144 B2 | 11/2009 | Bodduluri |
| 7,639,853 B2 | 12/2009 | Olivera et al. |
| 7,639,854 B2 | 12/2009 | Schnarr et al. |
| 7,643,661 B2 | 1/2010 | Ruchala et al. |
| 7,693,257 B2 | 4/2010 | Allison |
| 7,708,682 B2 | 5/2010 | Pekar et al. |
| 7,773,788 B2 | 8/2010 | Lu et al. |
| 7,801,349 B2 | 9/2010 | Wang et al. |
| 7,907,987 B2 | 3/2011 | Dempsey |
| 7,945,022 B2 | 5/2011 | Nelms et al. |
| 8,085,899 B2 | 12/2011 | Nord et al. |
| 8,125,813 B2 | 2/2012 | Nizin et al. |
| 2003/0072411 A1 | 4/2003 | Welsh |
| 2003/0212325 A1 | 11/2003 | Cotrutz et al. |
| 2004/0068182 A1 | 4/2004 | Misra |
| 2005/0096515 A1 | 5/2005 | Geng |
| 2005/0143965 A1 | 6/2005 | Failla et al. |
| 2005/0201516 A1 | 9/2005 | Ruchala et al. |
| 2006/0100738 A1 | 5/2006 | Alsafadi et al. |
| 2007/0041496 A1 | 2/2007 | Olivera et al. |
| 2007/0041498 A1 | 2/2007 | Olivera et al. |
| 2007/0197908 A1 | 8/2007 | Ruchala et al. |
| 2008/0008291 A1 | 1/2008 | Alakuijala et al. |
| 2008/0031406 A1 | 2/2008 | Yan et al. |
| 2008/0193006 A1 | 8/2008 | Udupa et al. |
| 2008/0279328 A1 | 11/2008 | Zeitler et al. |
| 2009/0110145 A1* | 4/2009 | Lu et al. ............... 378/65 |
| 2010/0053208 A1 | 3/2010 | Menningen et al. |
| 2010/0183121 A1* | 7/2010 | Riker et al. ............ 378/65 |
| 2011/0019889 A1 | 1/2011 | Gering et al. |
| 2011/0112351 A1 | 5/2011 | Fordyce et al. |

FOREIGN PATENT DOCUMENTS

| | | |
|---|---|---|
| JP | 11169471 | 6/1999 |
| JP | 2004166975 | 6/2004 |
| JP | 2004275636 | 10/2004 |
| JP | 2005518908 | 6/2005 |
| JP | 2007516743 | 6/2007 |
| KR | 20050073862 | 7/2005 |
| TW | 300853 | 3/1997 |
| WO | 9014129 | 11/1990 |
| WO | 03076003 | 9/2003 |
| WO | 03092789 | 11/2003 |
| WO | 2004057515 | 7/2004 |
| WO | 2005035061 | 4/2005 |
| WO | 2005057463 | 6/2005 |
| WO | 2005062790 | 7/2005 |

OTHER PUBLICATIONS

Yu, Cedric X., et al., "A Method for Implementing Dynamic Photon Beam Intensity Modulation using Independent Jaws and a Multileaf Collimator," Phys. Med. Biol. 40. 1995: 769-787.

Yan, Di, "On-line Strategy of Daily Dose Prescription in Adaptive Radiotherapy," Proceedings of the 22nd Annual EMBS International Conference, Jul. 23-28, 2000, Chicago, IL, pp. 2145-2148.

Lee, Jason et al., "Intensity Modulated Radiation Therapy; An Introduction for Patients and Clinicians," www.oncolink.com/templates/treatment/article.cfm?c=45&s=33&id=182; Jun. 16, 2001.

Keall, Paul, "4-Dimensional Computed Tomography Imaging and Treatment Planning," Seminars in Radiation Oncology, vol. 14, No. 1, Jan. 2004; pp. 81-90.

Lof, J. et al., "An Adaptive Control Algorithm for Optimization of Intensity Modulated Radiotherapy Considering Uncertainties in Beam Profiles, Patient Set-Up and Internal Organ Motion", Physics in Medicine and Biology 43, 1605-1628, Printed in the UK, 1998.

Mackie, T. Rockwell et al., "Tomotherapy" Seminars in Radiation Oncology, vol. 9, No. 1, Jan. 1, 1999, pp. 108-117, XP002603992.

Miller, Karen, "The Phantom Torso", RT Image, vol. 14 No. 25, Jun. 18, 2001.

(56) References Cited

OTHER PUBLICATIONS

Rueckert, D. et al., "Nonrigid Registration Using Free-Form Deformations: Application to Breast MR Images", IEEE Transactions on Medical Imaging, vol. 18, No. 8, pp. 712-721, Aug. 1999.
Mackie, T. Rockwell et al., "Tomotherapy: Rethinking the Processes of Radiotherapy," XIIth ICCR, May 27-30, 1997.
Fang, Guang Y. et al., "Software system for the UW/GE tomotherapy prototype," Xiith ICCR, May 27-30, 1997.
PCT/US2009/055419 International Search Report and Written Opinion dated Apr. 12, 2010.
Office Action from Chinese Patent Office for Application No. 200980133932.0 dated Jan. 5, 2012.

* cited by examiner

SYSTEM AND METHOD OF CALCULATING DOSE UNCERTAINTY

RELATED APPLICATIONS

This application is a divisional of U.S. patent application Ser. No. 12/550,184, filed on Aug. 28, 2009, which is a non-provisional application of and claims priority to U.S. Provisional Patent Application No. 61/092,523, filed on Aug. 28, 2008. The entire contents of these applications are incorporated herein by reference.

BACKGROUND OF THE INVENTION

Over the past decades improvements in computers and networking, radiation therapy treatment planning software, and medical imaging modalities (CT, MRI, US, and PET) have been incorporated into radiation therapy practice. These improvements have led to the development of image guided radiation therapy ("IGRT"). IGRT is radiation therapy that uses cross-sectional images of the patient's internal anatomy to better target the radiation dose in the tumor while reducing the radiation exposure to healthy organs. The radiation dose delivered to the tumor is controlled with intensity modulated radiation therapy ("IMRT"), which involves changing the size, shape, and intensity of the radiation beam to conform to the size, shape, and location of the patient's tumor. IGRT and IMRT lead to improved control of the tumor while simultaneously reducing the potential for acute side effects due to irradiation of healthy tissue surrounding the tumor.

SUMMARY OF THE INVENTION

IMRT is a state-of-the-art technique for administering radiation to cancer patients. The goal of a treatment is to deliver a prescribed amount of radiation to a tumor, while limiting the amount absorbed by the surrounding healthy organs. Planning an IMRT treatment requires determining fluence maps, each consisting of hundreds or more beamlet intensities.

Several mathematical problems arise in order to optimally administer IMRT. Treatment proceeds by rotating the linac around the patient and coordinating the leaf movements in the MLC so that the radiation delivered conforms to some desirable dose distribution at each gantry (beam) angle.

In addition to knowing the beam angles, one must also know how intense the beams should be at each point (x, y) on the MLC aperture for all gantry angles. These intensity profiles, or fluence maps, are represented by two-dimensional, nonnegative functions $Ia(x, y)$ for $a=1, 2, \ldots, k$, where k is the number of gantry angles in use. The process of determining the functions $Ia(x, y)$ is often called fluence map optimization. Finally, once the fluence maps $Ia(x, y)$ are determined, one must convert these into MLC leaf sequences that attempt to realize them. The longer an MLC leaf is open at a certain position (x, y), the more dose the tissue along a straight path from that position (plus some surrounding tissue) absorbs. The process of converting fluence maps into the opening and closing movements of leaves is called leaf-sequencing. There are many physical and mathematical issues that affect how successful MLC leaf sequences are at approximating the desired fluence maps.

From a treatment planning perspective, TomoTherapy® treatment technology allows for tremendous flexibility when treating complicated target volumes due to the large number of projections (beam angles) that can be used. The TomoTherapy® system has the ability to deliver radiation helically to the patient. The unique nature of the helical delivery pattern however, requires the user to specify new planning parameters such as field width, pitch, and modulation factor. Failure to select judicious values for these parameters may compromise treatment plan quality, and may increase the total treatment time, as well as produce treatment plans which are more difficult for the radiation delivery device to accurately deliver.

In one embodiment, the invention provides a method of evaluating dosimetric uncertainties for a radiation delivery. The method includes generating a treatment plan for a patient, the treatment plan including a dose to be delivered to the patient using a radiation delivery device; identifying a data parameter for the radiation delivery device; and generating a variance map utilizing a dose calculation module, the variance map representing an uncertainty indication in the dose to be delivered to the patient, the uncertainty indication related to the data parameter.

In another embodiment, the invention provides a method of detecting a delivery error in a radiation delivery device. The method includes generating a treatment plan for a patient, the treatment plan including an intended fluence; delivering radiation to the patient according to the treatment plan; acquiring output fluence information from the radiation delivery device after delivery of the treatment plan; comparing the output fluence information and the intended fluence to determine a fluence variance; and applying a dose calculation algorithm to the fluence variance to generate a dose variance map.

In a further embodiment, the invention provides a method of evaluating a partially delivered treatment plan. The method includes generating a treatment plan for a patient, the treatment plan including a plurality of treatment fractions and intended variance information; delivering at least one of the treatment fractions to the patient according to the treatment plan; acquiring output fluence information from a radiation delivery device after delivery of the treatment fraction; and evaluating future treatment fractions based on a combination of the intended variance information and the output fluence information.

Other aspects of the invention will become apparent by consideration of the detailed description and accompanying drawings.

DETAILED DESCRIPTION OF THE INVENTION

Figure 1:
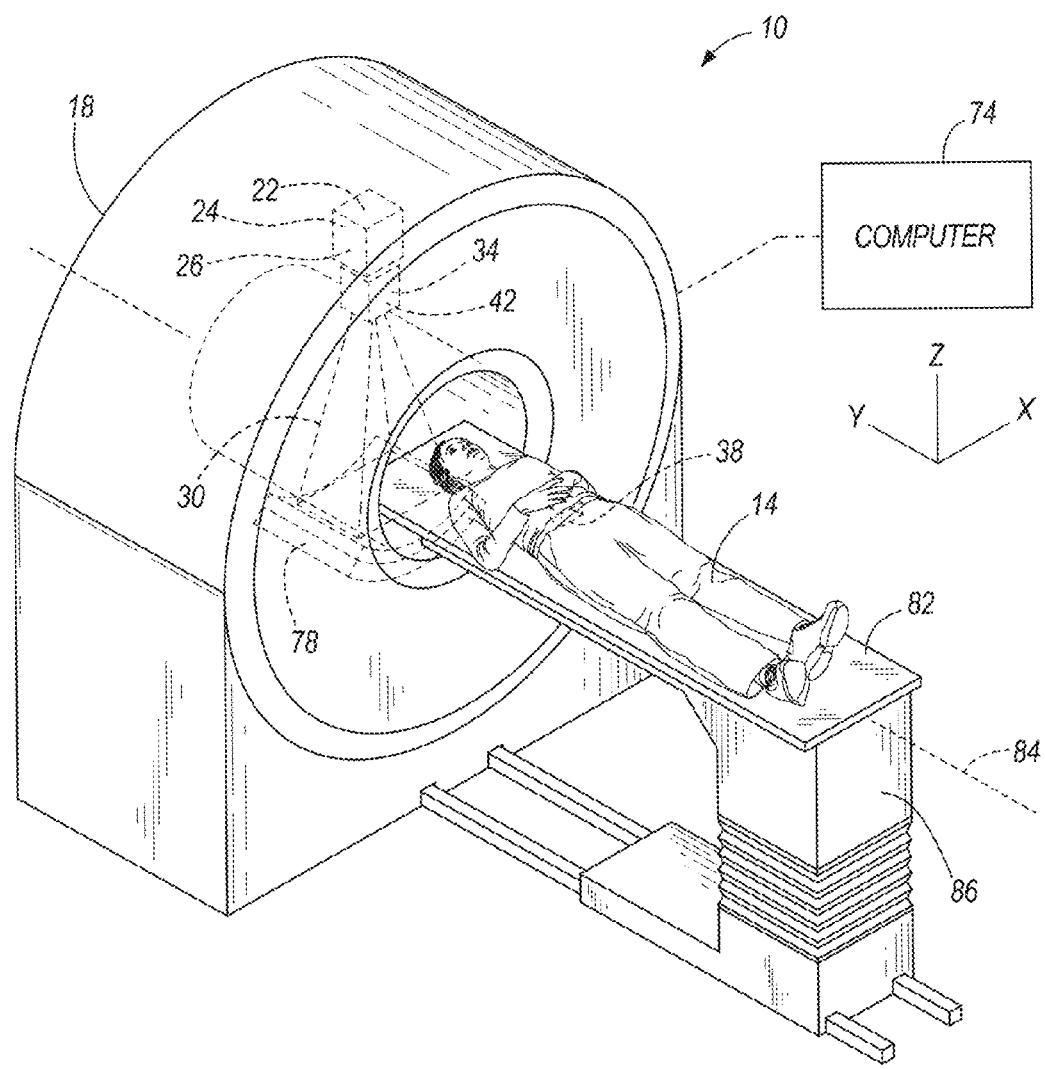
FIG. 1 is a perspective view of a radiation therapy treatment system.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings.

Although directional references, such as upper, lower, downward, upward, rearward, bottom, front, rear, etc., may be made herein in describing the drawings, these references are made relative to the drawings (as normally viewed) for convenience. These directions are not intended to be taken literally or limit the present invention in any form. In addition, terms such as "first," "second," and "third" are used herein for purposes of description and are not intended to indicate or imply relative importance or significance.

In addition, it should be understood that embodiments of the invention include both hardware, software, and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the invention may be implemented in software. As such, it should be noted that a plurality of hardware and software based devices, as well as a plurality of different structural components may be utilized to implement the invention. Furthermore, and as described in subsequent paragraphs, the specific mechanical configurations illustrated in the drawings are intended to exemplify embodiments of the invention and that other alternative mechanical configurations are possible.

FIG. 1 illustrates a radiation therapy treatment system 10 that can provide radiation therapy to a patient 14. The radiation therapy treatment can include photon-based radiation therapy, brachytherapy, electron beam therapy, proton, neutron, or particle therapy, or other types of treatment therapy. The radiation therapy treatment system 10 includes a gantry 18. The gantry 18 can support a radiation module 22, which can include a radiation source 24 and a linear accelerator 26 operable to generate a beam 30 of radiation. Though the gantry 18 shown in the drawings is a ring gantry, i.e., it extends through a full 360° arc to create a complete ring or circle, other types of mounting arrangements may also be employed. For example, a non-ring-shaped gantry, such as a C-type, partial ring gantry, or robotic arm could be used. Any other framework capable of positioning the radiation module 22 at various rotational and/or axial positions relative to the patient 14 may also be employed. In addition, the radiation source 24 may travel in path that does not follow the shape of the gantry 18. For example, the radiation source 24 may travel in a non-circular path even though the illustrated gantry 18 is generally circular-shaped.

The radiation module 22 can also include a modulation device 34 operable to modify or modulate the radiation beam 30. The modulation device 34 provides the modulation of the radiation beam 30 and directs the radiation beam 30 toward the patient 14. Specifically, the radiation beam 34 is directed toward a portion of the patient. Broadly speaking, the portion may include the entire body, but is generally smaller than the entire body and can be defined by a two-dimensional area and/or a three-dimensional volume. A portion desired to receive the radiation, which may be referred to as a target 38 or target region, is an example of a region of interest. Another type of region of interest is a region at risk. If a portion includes a region at risk, the radiation beam is preferably diverted from the region at risk. The patient 14 may have more than one target region that needs to receive radiation therapy. Such modulation is sometimes referred to as intensity modulated radiation therapy ("IMRT").

Figure 2:
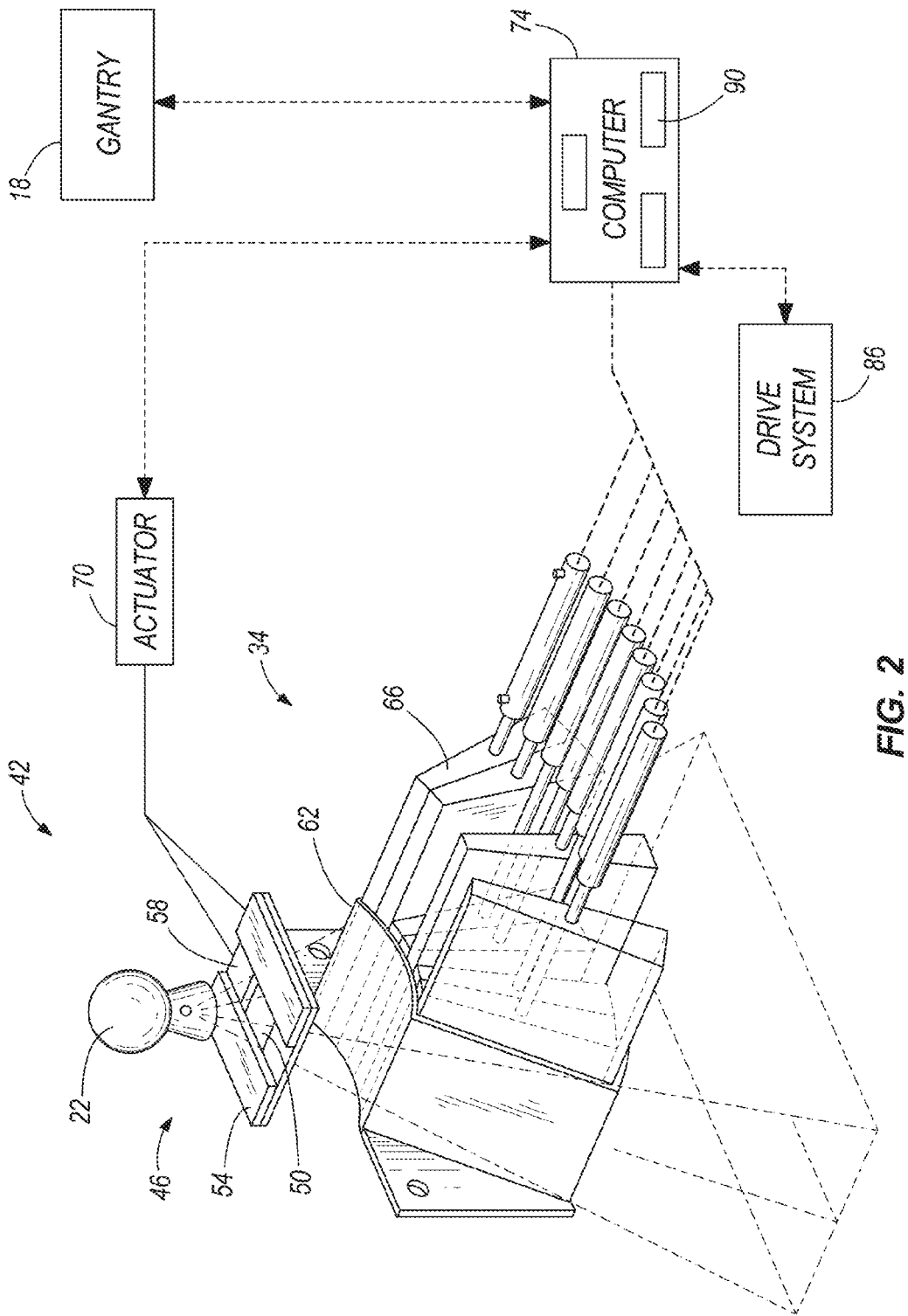
FIG. 2 is a perspective view of a multi-leaf collimator that can be used in the radiation therapy treatment system illustrated in FIG. 1.

The modulation device 34 can include a collimation device 42 as illustrated in FIG. 2. The collimation device 42 includes a set of jaws 46 that define and adjust the size of an aperture 50 through which the radiation beam 30 may pass. The jaws 46 include an upper jaw 54 and a lower jaw 58. The upper jaw 54 and the lower jaw 58 are moveable to adjust the size of the aperture 50.

In one embodiment, and illustrated in FIG. 2, the modulation device 34 can comprise a multi-leaf collimator 62, which includes a plurality of interlaced leaves 66 operable to move from position to position, to provide intensity modulation. It is also noted that the leaves 66 can be moved to a position anywhere between a minimally and maximally-open position. The plurality of interlaced leaves 66 modulate the strength, size, and shape of the radiation beam 30 before the radiation beam 30 reaches the target 38 on the patient 14. Each of the leaves 66 is independently controlled by an actuator 70, such as a motor or an air valve so that the leaf 66 can open and close quickly to permit or block the passage of radiation. The actuators 70 can be controlled by a computer 74 and/or controller.

The radiation therapy treatment system 10 can also include a detector 78, e.g., a kilovoltage or a megavoltage detector, operable to receive the radiation beam 30. The linear accelerator 26 and the detector 78 can also operate as a computed tomography (CT) system to generate CT images of the patient 14. The linear accelerator 26 emits the radiation beam 30 toward the target 38 in the patient 14. The target 38 absorbs some of the radiation. The detector 78 detects or measures the amount of radiation absorbed by the target 38. The detector 78 collects the absorption data from different angles as the linear accelerator 26 rotates around and emits radiation toward the patient 14. The collected absorption data is transmitted to the computer 74 to process the absorption data and to generate images of the patient's body tissues and organs. The images can also illustrate bone, soft tissues, and blood vessels.

The CT images can be acquired with a radiation beam 30 that has a fan-shaped geometry, a multi-slice geometry or a cone-beam geometry. In addition, the CT images can be acquired with the linear accelerator 26 delivering megavoltage energies or kilovoltage energies. It is also noted that the acquired CT images can be registered with previously acquired CT images (from the radiation therapy treatment system 10 or other image acquisition devices, such as other CT scanners, MRI systems, and PET systems). For example, the previously acquired CT images for the patient 14 can include identified targets 38 made through a contouring process. The newly acquired CT images for the patient 14 can be registered with the previously acquired CT images to assist in identifying the targets 38 in the new CT images. The registration process can use rigid or deformable registration tools.

The image data can be presented on a video display as either a three-dimensional image or a series of two-dimensional images. In addition, the image data comprising the images can be either voxels (for three-dimensional images) or pixels (for two-dimensional images). The term image element is used generally in the description to refer to both.

In some embodiments, the radiation therapy treatment system 10 can include an x-ray source and a CT image detector. The x-ray source and the CT image detector operate in a similar manner as the linear accelerator 26 and the detector 78 as described above to acquire image data. The image data is transmitted to the computer 74 where it is processed to generate images of the patient's body tissues and organs.

The radiation therapy treatment system 10 can also include a patient support, such as a couch 82 (illustrated in FIG. 1), which supports the patient 14. The couch 82 moves along at least one axis 84 in the x, y, or z directions. In other embodiments of the invention, the patient support can be a device that is adapted to support any portion of the patient's body. The patient support is not limited to having to support the entire patient's body. The system 10 also can include a drive system 86 operable to manipulate the position of the couch 82. The drive system 86 can be controlled by the computer 74.

Figure 3:
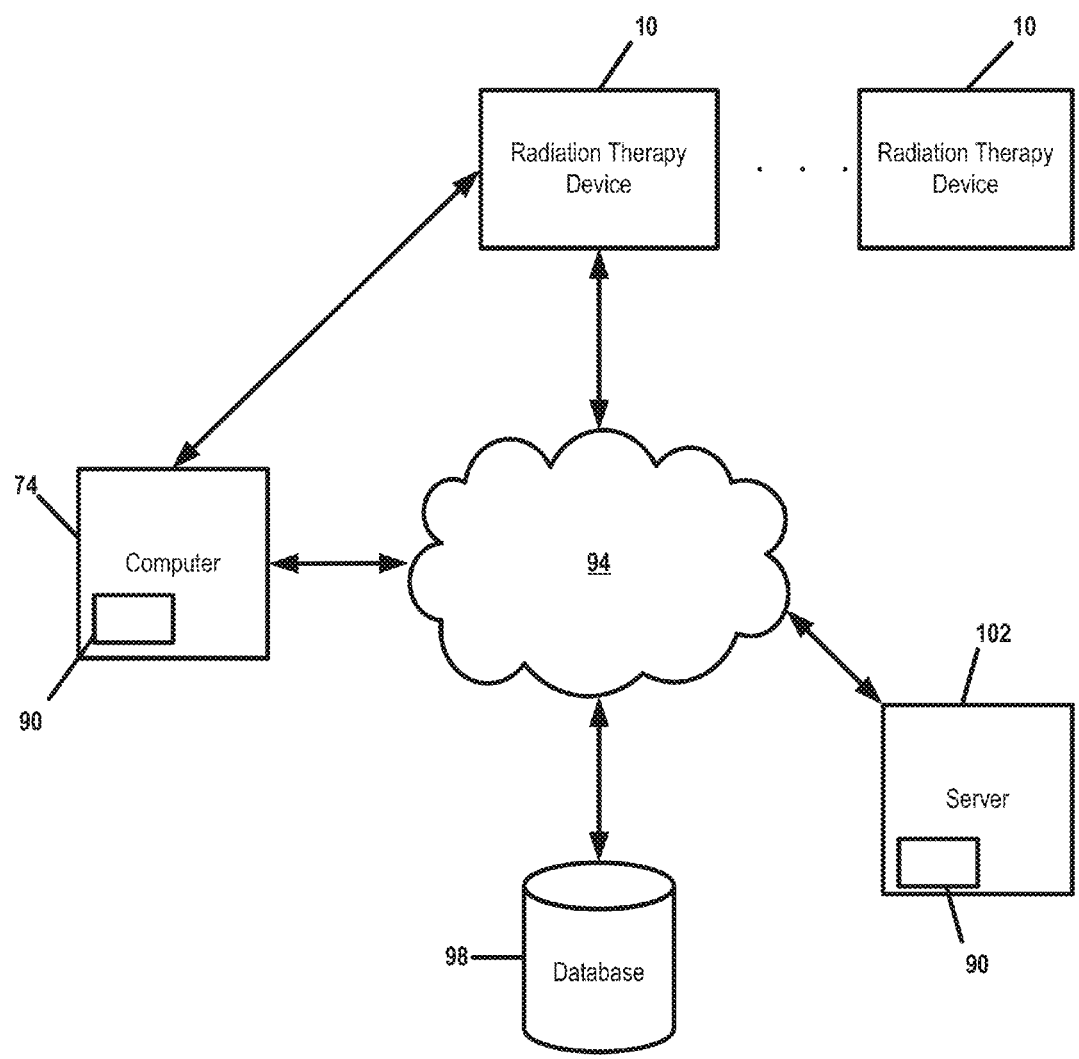
FIG. 3 is a schematic illustration of the radiation therapy treatment system of FIG. 1.
Figure 4:
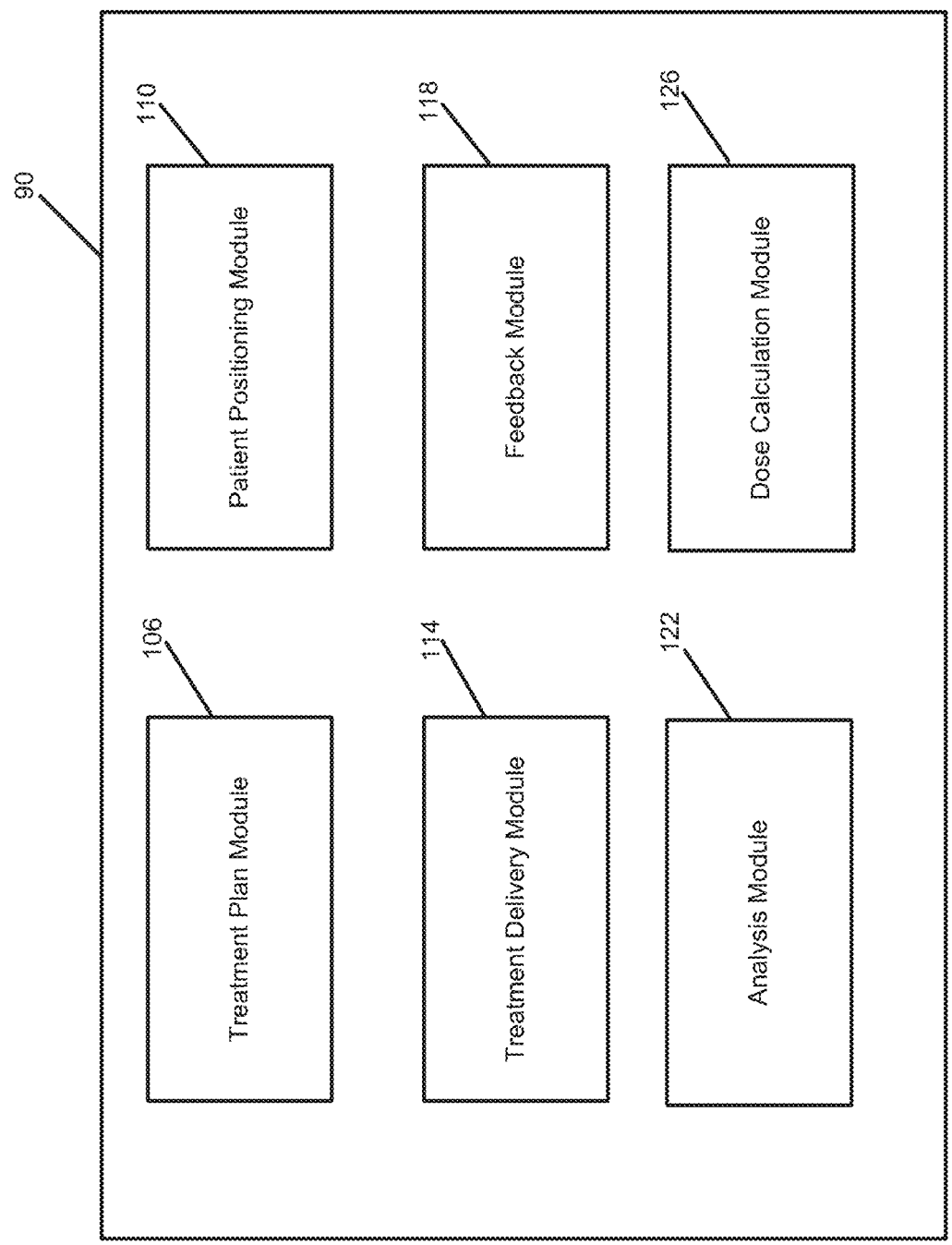
FIG. 4 is a schematic diagram of a software program used in the radiation therapy treatment system.

The computer 74, illustrated in FIGS. 2 and 3, includes an operating system for running various software programs and/or a communications application. In particular, the computer 74 can include a software program(s) 90 that operates to communicate with the radiation therapy treatment system 10. The computer 74 can include any suitable input/output device adapted to be accessed by medical personnel. The computer 74 can include typical hardware such as a processor, I/O interfaces, and storage devices or memory. The computer 74 can also include input devices such as a keyboard and a mouse. The computer 74 can further include standard output devices, such as a monitor. In addition, the computer 74 can include peripherals, such as a printer and a scanner.

The computer 74 can be networked with other computers 74 and radiation therapy treatment systems 10. The other computers 74 may include additional and/or different computer programs and software and are not required to be identical to the computer 74, described herein. The computers 74 and radiation therapy treatment system 10 can communicate with a network 94. The computers 74 and radiation therapy treatment systems 10 can also communicate with a database(s) 98 and a server(s) 102. It is noted that the software program(s) 90 could also reside on the server(s) 102.

The network 94 can be built according to any networking technology or topology or combinations of technologies and topologies and can include multiple sub-networks. Connections between the computers and systems shown in FIG. 3 can be made through local area networks ("LANs"), wide area networks ("WANs"), public switched telephone networks ("PSTNs"), wireless networks, Intranets, the Internet, or any other suitable networks. In a hospital or medical care facility, communication between the computers and systems shown in FIG. 3 can be made through the Health Level Seven ("HL7") protocol or other protocols with any version and/or other required protocol. HL7 is a standard protocol which specifies the implementation of interfaces between two computer applications (sender and receiver) from different vendors for electronic data exchange in health care environments. HL7 can allow health care institutions to exchange key sets of data from different application systems. Specifically, HL7 can define the data to be exchanged, the timing of the interchange, and the communication of errors to the application. The formats are generally generic in nature and can be configured to meet the needs of the applications involved.

Communication between the computers and systems shown in FIG. 3 can also occur through the Digital Imaging and Communications in Medicine (DICOM) protocol with any version and/or other required protocol. DICOM is an international communications standard developed by NEMA that defines the format used to transfer medical image-related data between different pieces of medical equipment. DICOM RT refers to the standards that are specific to radiation therapy data.

The two-way arrows in FIG. 3 generally represent two-way communication and information transfer between the network 94 and any one of the computers 74 and the systems 10 shown in FIG. 3. However, for some medical and computerized equipment, only one-way communication and information transfer may be necessary.

The software program 90 includes a plurality of modules that communicate with one another to perform functions of the radiation therapy treatment process. The various modules communication with one another to determine if delivery of the radiation therapy treatment plan occurred as intended.

The software program 90 includes a treatment plan module 106 operable to generate a treatment plan for the patient 14 based on data input to the system 10 by medical personnel. The data can include one or more images (e.g., planning images and/or pre-treatment images) of at least a portion of the patient 14 and a fluence map. The treatment plan module 106 separates the treatment into a plurality of fractions and determines the radiation dose for each fraction or treatment based on the prescription input by medical personnel. The treatment plan module 106 also determines the radiation dose for the target 38 based on various contours drawn around the target 38. Multiple targets 38 may be present and included in the same treatment plan.

The software program 90 also includes a patient positioning module 110 operable to position and align the patient 14 with respect to the isocenter of the gantry 18 for a particular treatment fraction. While the patient is on the couch 82, the patient positioning module 110 acquires an image of the patient 14 and compares the current position of the patient 14 to the position of the patient in a reference image. The reference image can be a planning image, any pre-treatment image, or a combination of a planning image and a pre-treatment image. If the patient's position needs to be adjusted, the patient positioning module 110 provides instructions to the drive system 86 to move the couch 82 or the patient 14 can be manually moved to the new position. In one construction, the patient positioning module 110 can receive data from lasers positioned in the treatment room to provide patient position data with respect to the isocenter of the gantry 18. Based on the data from the lasers, the patient positioning module 110 provides instructions to the drive system 86, which moves the couch 82 to achieve proper alignment of the patient 14 with respect to the gantry 18. It is noted that devices and systems, other than lasers, can be used to provide data to the patient positioning module 110 to assist in the alignment process.

The patient positioning module 110 also is operable to detect and/or monitor patient motion during treatment. The patient positioning module 110 may communicate with and/or incorporate a motion detection system 112, such as x-ray, in-room CT, laser positioning devices, camera systems, spirometers, ultrasound, tensile measurements, chest bands, and the like. The patient motion can be irregular or unexpected, and does not need to follow a smooth or reproducible path.

The software program 90 also includes a treatment delivery module 114 operable to instruct the radiation therapy treatment system 10 to deliver the treatment plan to the patient 14 according to the treatment plan. The treatment delivery module 114 can generate and transmit instructions to the gantry 18, the linear accelerator 26, the modulation device 34, and the drive system 86 to deliver radiation to the patient 14. The instructions coordinate the necessary movements of the gantry 18, the modulation device 34, and the drive system 86 according to a fluence map to deliver the radiation beam 30 to the proper target in the proper amount as specified in the treatment plan.

The treatment delivery module 114 also calculates the appropriate pattern, position, and intensity of the radiation beam 30 to be delivered, to match the prescription as specified by the treatment plan. The pattern of the radiation beam 30 is generated by the modulation device 34, and more particularly by movement of the plurality of leaves in the multi-leaf collimator. The treatment delivery module 114 can utilize canonical, predetermined or template leaf patterns to generate the appropriate pattern for the radiation beam 30 based on the treatment parameters. The treatment delivery module 114 can also include a library of patterns for typical cases that can be accessed in which to compare the present patient data to determine the pattern for the radiation beam 30.

The software program 90 also includes a feedback module 118 operable to receive data from the radiation therapy treatment system 10 during a patient treatment. The feedback module 118 can receive data from the radiation therapy treatment device and can include information related to patient transmission data, ion chamber data, fluence output data, MLC data, system temperatures, component speeds and/or positions, flow rates, etc. The feedback module 118 can also receive data related to the treatment parameters, amount of radiation dose the patient received, image data acquired during the treatment, and patient movement. In addition, the feedback module 118 can receive input data from a user and/or other sources. The feedback module 118 acquires and stores the data until needed for further processing.

The software program 90 also includes an analysis module 122 operable to analyze the data from the feedback module 118 to determine whether delivery of the treatment plan occurred as intended and to validate that the planned delivery is reasonable based on the newly-acquired data. The analysis module 122 can also determine, based on the received data and/or additional inputted data, whether a problem has occurred during delivery of the treatment plan. For example, the analysis module 122 can determine if the problem is related to an error of the radiation therapy treatment device 10, an anatomical error, such as patient movement, and/or a clinical error, such as a data input error.

The analysis module 122 can detect errors in the radiation therapy treatment device 10 related to the couch 82, the device output, the gantry 18, the multi-leaf collimator 62, the patient setup, and timing errors between the components of the radiation therapy treatment device 10. For example, the analysis module 122 can determine if a couch replacement was performed during planning, if fixation devices were properly used and accounted for during planning, if position and speed is correct during treatment.

The analysis module 122 can determine whether changes or variations occurred in the output parameters of the radiation therapy treatment device 10. With respect to the gantry 18, the analysis module 122 can determine if there are errors in the speed and positioning of the gantry 18. The analysis module 122 can receive data to determine if the multi-leaf collimator 62 is operating properly. For example, the analysis module 122 can determine if the leaves 66 move at the correct times, if any leaves 66 are stuck in place, if leaf timing is properly calibrated, and whether the leaf modulation pattern is correct for any given treatment plan. The analysis module 122 also can validate patient setup, orientation, and position for any given treatment plan. The analysis module 122 also can validate that the timing between the gantry 18, the couch 62, the linear accelerator 26, the leaves 66 are correct.

The software program 90 also includes a dose calculation module 126 operable to generate a variance map that represents a dose uncertainty. The dose calculation module 126 receives a density image (e.g., a patient CT image), the relative positions and motions of the radiation source ("source") with respect to the density image (position and motion is referred to as "plan geometry"), and a fluence map describing the fluence incident to a 2-D plane in front of the source at each moment in time. From these inputs (and others, such as machine commissioning) a dose image is calculated. The fluence map over time is replaced by a map of fluence uncertainty, error, or other metric. The dose calculation module 126 is run as usual, using the fluence uncertainty/error map like it would normally use the fluence map. The resulting image represents the uncertainty/error projected into image space, instead of a dose image.

For example, suppose we have a fluence map for a radiation treatment plan and a corresponding fluence map reconstructed after one delivery of that plan. The dose calculation module 126 generates a variance map by replacing the fluence map with the square of the difference between the planned and delivered fluence maps. The dose calculation module 126 is run using this variance map. The resulting image represents the variance in the dose to each image voxel, accumulated over the duration of the delivery. The square root of these variance values would be the standard deviation of delivered dose versus planned dose to each voxel over the duration of the delivery.

Uncertainty or error in plan geometry at a particular time can be represented as uncertainty in the fluence map over a neighboring time interval. For example, if there is uncertainty in the gantry position at some point in time (t), and the gantry is moving, then the fluence uncertainty for a nearby points in time (t') is affected by the probability that the gantry is at the position expected at that time (t').

There is a noted difference between projecting uncertainty/variance from the fluence map to image space versus comparing two dose images: multiple errors in a fluence map may cancel out in a normal dose calculation, so the error may not show up in the computed dose volume. But multiple errors projected through the dose calculation module 126 as variance (or a similar non-negative metric) are accumulated and do not cancel out. So, regions of dose uncertainty will be visible in the computed uncertainty volume.

The variance map generated by the dose calculation module 126 illustrates on a point-by-point basis where high uncertainty in the dose may exist and where low uncertainty in the dose may exist. The dose uncertainty is a result of an error in one or more data parameters related to a delivery parameter or a computational parameter. In other words, the dose uncertainty represents the effect of uncertainties in the planning and delivery of radiation to the patient. The dose uncertainty can be taken into consideration prospectively when planning a treatment plan for the patient and retrospectively to adjust or modify the treatment plan.

The dose uncertainty serves as a constraint when determining a setting of the data parameter(s). The data parameters related to delivery of radiation can include linac output, leaf timing, jaw position, spectral changes in attenuation/energy components of a radiation beam, couch position, and gantry position. Other data parameters related to modeling effects can include leaf size, leaf shape, jaw shape, tongue and groove information of two adjacent leaves, a source-to-axis distance, and a change in beam shape. The dose calculation module 126 can generate a dose variance map reflecting the effect on dose for a single data parameter. The dose calculation module 126 also can generate a dose variance map reflecting the effect on dose for a combination of data parameters. Because the variance is additive (var[total]=var[a]+var[b]+ . . . ), the dose calculation module 126 can combine (sum) the variance in fluence caused by many data parameters and generate a dose variance map.

The dose calculation module 126 allows the user to anticipate operation of the radiation delivery device and to incorporate device feedback, which includes the error(s) to modify the treatment plan. The dose calculation module 126 proactively accounts for mechanical variations of the device and how they may impact the treatment delivery.

Accordingly, the dose calculation module 126 can optimize a treatment plan to reduce the dose uncertainty by using the uncertainty indication to set one or more of the data parameters when preparing for treatment delivery. More specifically, the treatment plan can be optimized to reduce the uncertainty in dose for a particular area in the patient as shown on the dose variance map. In addition, the treatment plan can be modified to account for the dose variance map, a different radiation delivery device can be selected to deliver the treatment, and an entirely different treatment plan can be generated or chosen from a list of alternate plans previously generated.

The dose calculation module 126 also can optimize the treatment plan to reduce dose uncertainty by reducing the treatment plan's dependence on MLC leaves that have higher uncertainty (e.g., if a leaf is starting to go fall out of tolerance, we can generate treatment plans that use it less often), adjusting the treatment plan isocenter to reduce the impact of MLC or jaw positional uncertainties, adjusting the fraction of leaf open time in projections to reduce leaf timing uncertainties—leaf timing uncertainties are larger when a leaf has a very short open time or an open time nearly as long as the projection time, and/or reducing the treatment plan's dependence on gantry angles that have higher machine output uncertainty or shoot through regions of space that are affected by couch top position uncertainty.

The dose calculation module 126 also can evaluate the deliverability of an optimized treatment plan. For example, the dose calculation module 126 can recommend that a different radiation delivery device be used to deliver the treatment plan to the patient. The dose calculation module 126 also can generate an alert to the user when the dose variance map indicates that the uncertainty in dose exceeds a predetermined threshold. The alert can be the basis for a number of decisions by the user, including selecting a different plan, reoptimizing the current plan, adjusting patient position or machine parameters, or performing repairs or maintenance on the delivery device.

In a retrospective analysis, the dose calculator 126 can detect a delivery error in the radiation delivery device. To do so, the dose calculator 126 can receive exit data from the radiation delivery device after delivery of the treatment plan. The exit data (e.g., output fluence information) can come from a detector such as, for example, a single-row gas ionization detector (e.g., xenon), a multi-row gas ionization detector, a crystal detector, a solid state detector, a flat panel detector (e.g., Amorphous silicon or selenium), or other suitable detecting devices. The dose calculator 126 can compare an intended fluence, which was specified in the treatment plan, with the output fluence information to generate a fluence variance. The dose calculator 126 uses the fluence variance as an input to a dose calculation algorithm to generate a dose variance map. The dose variance map can be displayed to the user.

The fluence variance can be based on feedback from the radiation delivery device over the course of a plurality of treatment fractions. Based on the fluence variance, the treatment plan can be modified, a new treatment plan can be generated, and/or a different radiation delivery device may be selected to deliver the remaining treatment fractions.

The dose calculation module 126 also can evaluate a partially delivered treatment plan to determine how pre-treatment variance risk is actually realized by looking at actual variances. A treatment plan is generated that includes a plurality of treatment fractions and intended variance information. After delivery of at least one of the treatment fractions, the dose calculation module 126 acquires output fluence information from the radiation delivery device. The dose calculation module 126 can evaluate future treatment fractions and assess the risk of treatment plan deviation for future treatments based upon a combination of the intended variance information and the measured variance information. Based on that risk, the user can decide whether to proceed with the plan, whether to reoptimize the plan, whether to choose a different plan to deliver, or whether other delivery options exist.

EXAMPLE

Purpose: To investigate the source of delivery quality assurance (DQA) errors observed for a subset of patients planned for treatment on TomoTherapy® treatment systems.

Method and Materials: Six patients planned on TomoTherapy® systems were selected for analysis. Three patients had passing DQA plans and three had DQA plans with ion-chamber measurements that deviated from the expected dose by more than 3%. The patients were planned using similar parameters, including a 2.5 cm field width and pitch values ranging from 0.143-0.215. Machine output was determined not to be a problem so normalized leaf timing sinograms were analyzed to determine the mean leaf open-time for each plan. This analysis suggests the observed discrepancies are associated with plans having predominantly low LOTs. To test this, patients with out of tolerance DQA measurements were replanned using an increased pitch of 0.287. After replanning, new DQA plans were generated and ion-chamber measurements performed. Exit fluence data was also collected during the DQA delivery using the onboard MVCT detectors for dose reconstruction purposes.

Results: Sinogram analysis showed increases in mean leaf open-times of 30-85% for the higher pitch plans. In addition, ion-chamber measurements showed a reduction in point dose errors of 1.9-4.4%, bringing the patient plans within the ±3% acceptance criteria. Dose reconstruction results were in excellent agreement with ion-chamber measurements and clearly illustrate the impact of leaf timing errors on plans having predominantly small leaf open-times.

Conclusion: The impact of leaf timing errors on treatment plans with low mean leaf open-times can be significant. This becomes important for treatment plans using low pitches, or potentially for hyperfractionated treatment schedules. The ability to reduce the impact of these delivery errors by increasing the treatment plan pitch is demonstrated. In addition, the efficacy of dose reconstruction in diagnosing delivery errors is established.

Discussion: This work arose out of a clinical situation where a subset of patients being planned for treatment on TomoTherapy® systems had patient specific delivery QA (DQA) point dose measurements that failed to meet the ±3% acceptance criteria set by our institution. Typical sources of DQA error such as phantom misalignment and machine output variation were eliminated from the list of possible causes by utilizing onboard MVCT imaging for setup verification, and by alternating measurements of failing DQA plans with passing plans having similar plan parameters—always observing the same result with a near constant dose rate.

To diagnose this issue, six patients planned for treatment on TomoTherapy® treatment systems were selected for analysis: three with plans that passed DQA and three with ion-chamber measurements that deviated from the expected values by more than 3%. All plans had similar parameters including a 2.5 cm field width and 15 sec gantry period. Pitch values—defined as the couch distance traveled per gantry rotation divided by the field width, were also similar and ranged from 0.143-0.215. For each patient plan, normalized leaf timing sinograms—which contain information about the amount of time each leaf of the MLC is open relative to the total projection time, were obtained from the treatment planning system and read into MATLAB for analysis. Mean fractional leaf open-times were computed and are listed in Table 1 along with other treatment plan parameters and DQA point dose results.

As seen from Table 1, the out of tolerance DQA treatment plans have considerably lower mean leaf open-times. Based on this result it was hypothesized that increasing the mean leaf open time for patients 1-3 in Table 1 would result in a reduction in the error seen in the DQA measurements. To test this hypothesis, patients 1-3 were replanned with an increased pitch of 0.287. Increasing the pitch effectively increases the mean leaf open-time by forcing the same prescription dose to be delivered in fewer rotations. After replanning, new DQA treatment plans were generated and ion-chamber measurements were performed. In addition to DQA ion-chamber measurements, exit fluence data was also collected using the onboard MVCT detectors during the delivery of both the original and replanned DQA procedures. Using tools developed by TomoTherapy Inc., this data was utilized to reconstruct delivered fluence sinograms by looking at the signal profile of the individual detector channels taken over the time of each projection. These sinograms were then used to reconstruct the delivered dose in the DQA phantom image.

TABLE 1

Patient plan parameters and DQA measurement data

| Patient data | | | Plan parameters | | DQA dose errors | |
|---|---|---|---|---|---|---|
| Patient | Disease site | Dose/fx (Gy) | Pitch | Mean fractional leaf time | Planned dose (Gy) | Discrepancy (%) |
| 1 | Head and neck | 2.12 | 0.143 | 0.196 | 1.589 | 4.47 |
| 2 | Thorax | 1.80 | 0.215 | 0.304 | 1.448 | 3.59 |
| 3 | Thyroid | 2.00 | 0.215 | 0.285 | 1.391 | 4.96 |
| 4 | Lung | 3.00 | 0.215 | 0.519 | 2.651 | −0.53 |
| 5 | Prostate | 2.50 | 0.172 | 0.448 | 2.877 | −0.48 |
| 6 | Pelvis | 3.00 | 0.215 | 0.472 | 2.487 | −0.16 |

Figure 5:
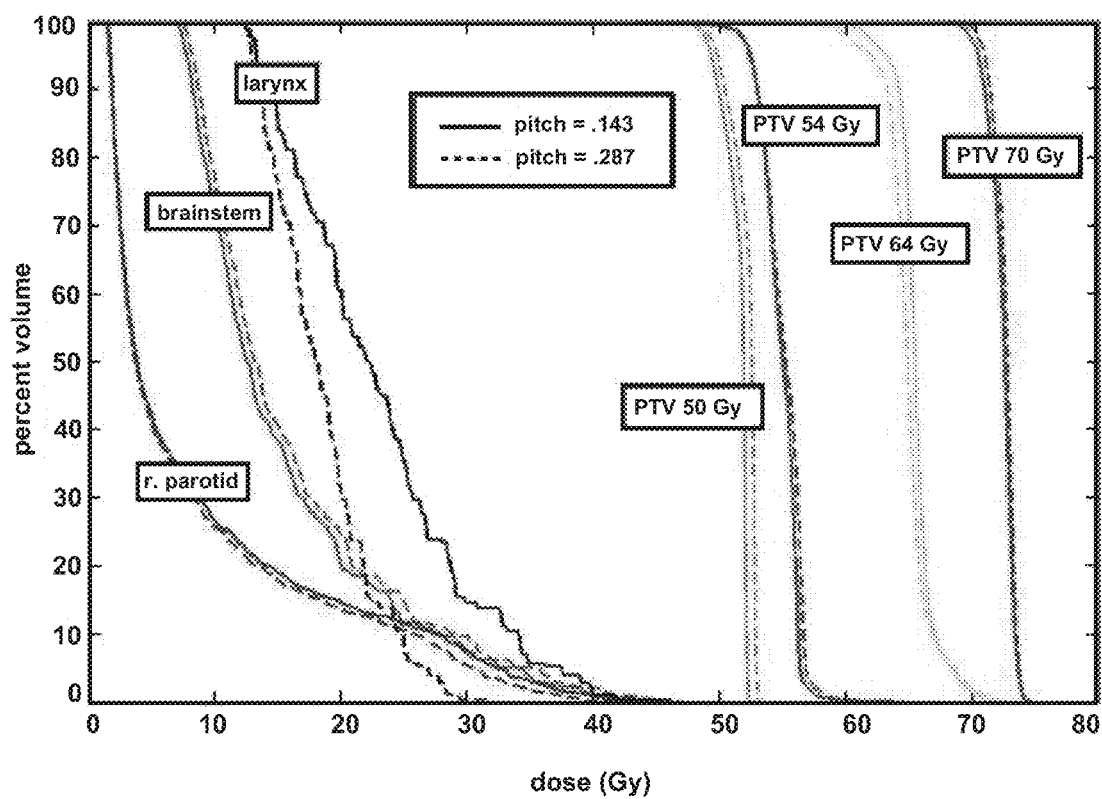
FIG. 5 illustrates dose volume histograms for a representative patient replanned using an increased pitch.
Figure 6:
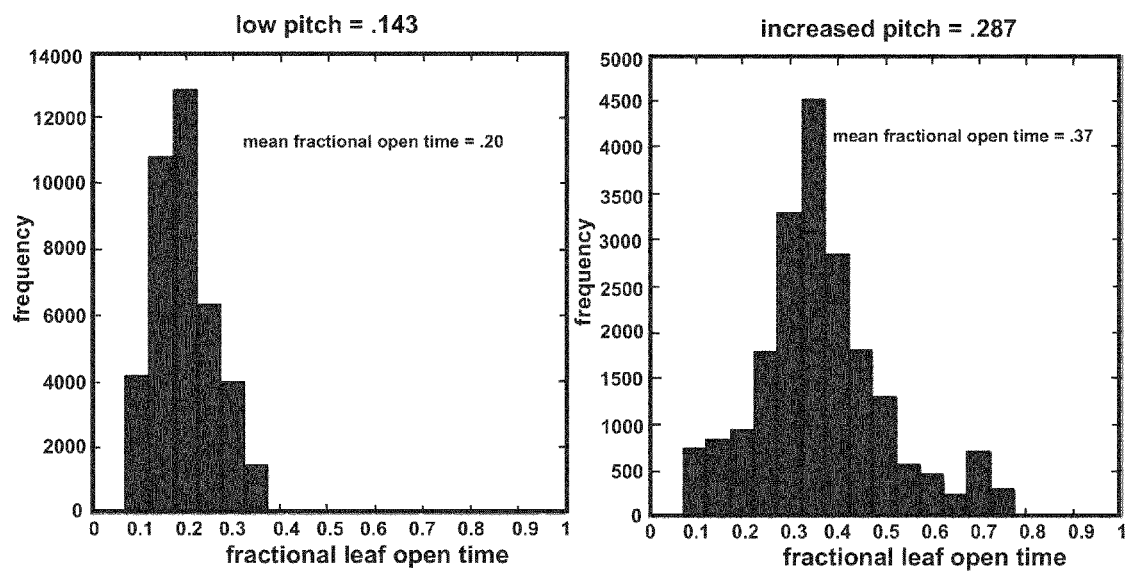
FIG. 6 illustrates histograms of the normalized leaf open-times both before and after replanning.
Figure 7:
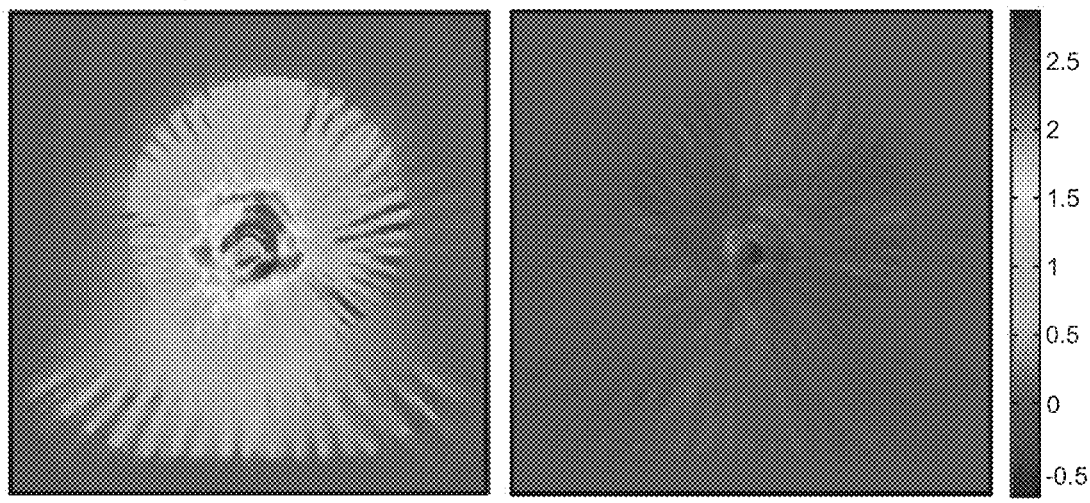
FIG. 7 illustrates slices of variance maps taken between the reconstructed and planned DQA dose grids for both the low and high pitch plans.
Figure 8:
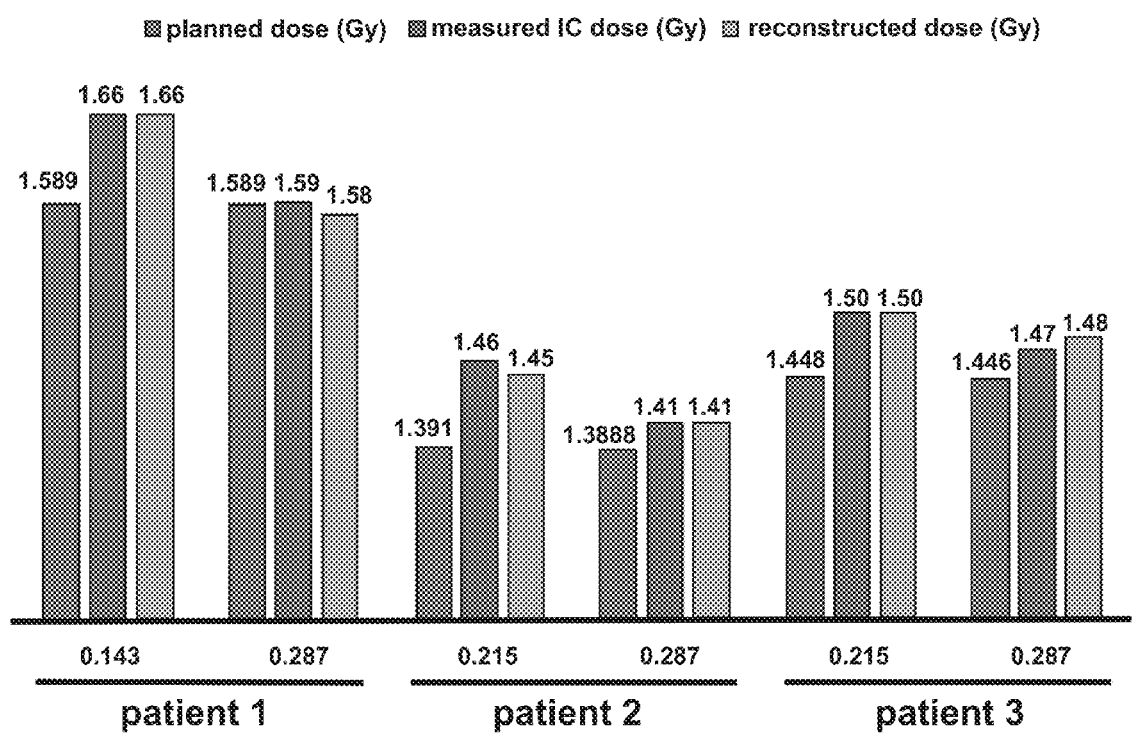
FIG. 8 illustrates the results of ion-chamber measurements made both before and after replanning, and indicates a reduction in error with the high pitch plans.

FIG. 5 shows dose volume histograms for a representative patient replanned using an increased pitch of 0.287, while FIG. 6 shows histograms of the normalized leaf open times both before and after replanning. These figures illustrate that while near equivalent plans are achieved using the two different pitch values, the mean leaf open time is increased by a factor of 1.85 for the increased pitch plan. FIG. 7 shows slices of difference maps taken between the reconstructed and planned DQA dose grids for both the low and high pitch plans. These difference maps are taken in the plane of the DQA ion-chamber measurements and illustrate the impact of leaf timing errors when treating plans that use predominantly low leaf open-times. This result is likely due to the greater importance of individual leaf latency errors when the total leaf open time is small, as well as the non-linear behavior of the MLC leaves when operating at very short leaf open times. FIG. 8 shows the results of ion-chamber measurements made both before and after replanning, and indicates a reduction in error with the high pitch plans ranging from 1.9-4.4% for the three patients examined. Reconstructed dose values are also included in this figure and show excellent agreement with measured values for all plans delivered.

The example presented above tells us that for the radiation therapy plans described therein, there was an error in the fluence map identified that is not related to the plan itself. In one particular case, it is identified as a leaf open time error. As discussed in more detail below, one aspect of the invention includes a method of transferring that fluence uncertainty into something visual. In essence, the invention includes a method of using dose calculation as a means to visualize uncertainty (i.e., visualize errors in the fluence map by transforming those errors into errors in dose). We can take a collection of error sources (such as MLC errors, linac output variation, delivery uncertainties, gantry motion, beam trajectory through the patient, couch motion, IVDT/density uncertainties, machine calibration parameters, etc.) and use the dose calculator to combine the errors like dose to make an error or variance map. Leaf open time, as discussed herein, is one possible error that can be identified and calculated according to this method.

In one embodiment, the method includes replacing the fluence map with an uncertainty (error or variance) map and sending the uncertainty indication through the dose calculator to get a dose uncertainty. In this way, the variance is distributed in real space (ray tracing from sinogram space into patient space). Then, a convolution algorithm can be applied to the variance and in some embodiments, optimize the plan with respect to the uncertainty indication.

In one particular example, a treatment plan's sensitivity to delivery or modeling errors in the fluence map can be evaluated by generating a variance (or error) map post-delivery throughout the treatment volume. In principle, this approach can be usable for investigating any type of delivery or modeling error that can be estimated on a per-beamlet basis. One type of potential delivery error is related to a leaf open-time parameter, which is discussed below.

Certain treatment plans can be sensitive to short leaf open-time errors. In one example, one leaf was consistently about 6 ms "hot". A leaf open-time error generally manifests itself as a dose error for treatment plans with predominantly short leaf open-times using (in this case) the "hot" leaf. However, it is not necessarily the case that all treatment plans with a significant number of short leaf open-time beamlets will have dose errors. For example, if the short leaf open-time beamlets (and their associated errors) are distributed throughout the dose volume the effect in any one region may be negligible. Conversely, a treatment plan with relatively small number of short leaf open-time beamlets might show a significant dose error if many of those beamlets dominate the dose in one location.

In order to evaluate a treatment plan for sensitivity to delivery errors (e.g., short leaf open-times) it is necessary to generate a map of delivery error throughout the treatment volume. This is substantially similar to the computation that the dose calculator does. If we substitute an estimate of delivery error (variance) for fluence at each beamlet then the dose calculator will generate a variance map. Other changes in the parameters supplied to the dose calculator will be required (e.g., elimination of adjacent-leaf corrections), but preliminary discussions turned up no significant implementation issues.

The most accurate estimate of dose error would come from a machine-specific leaf open-time error measurement. However, since leaf behavior may change over time it would probably be best to use a generic "worst-case" estimate of leaf open-time error to identify treatment plans that could be problematic in general.

Note that the units of variance supplied to the dose calculator should be directly proportional to fluence so the contributions from multiple beamlets can sum like the dose would. In the case of leaf open-time errors, that would be time (instead of the unit-less percent LOT error, for example). If a percent-error is desired, that calculation can occur after the error is summed.

Various features and advantages of the invention are set forth in the following claims.

What is claimed is:

1. A method of detecting a delivery error in a radiation delivery device, the method comprising using a computer to carry out the steps of:
    generating a treatment plan for a patient, the treatment plan including an intended fluence;
    delivering radiation to the patient according to the treatment plan;
    acquiring output fluence information from the radiation delivery device after delivery of the treatment plan;
    comparing the output fluence information and the intended fluence to determine a fluence variance; and
    applying a dose calculation algorithm to the fluence variance to generate a dose variance map.

2. The method of claim 1 wherein the fluence variance is based on feedback from the radiation delivery device over the course of a plurality of treatments.

3. The method of claim 1 further comprising modifying the treatment plan based on the fluence variance.

4. The method of claim 1 further comprising generating a new treatment plan based on the fluence variance.

5. The method of claim 1 further comprising selecting a different radiation delivery device to deliver the treatment plan based on the fluence variance.

6. The method of claim 1 further comprising modifying the treatment plan based on anticipated changes to the radiation delivery device.

7. The method of claim 1 further comprising displaying the dose variance map.

8. The method of claim 1 wherein the dose variance map represents an uncertainty indication in the dose to be delivered to the patient, the uncertainty indication related to a data parameter of the radiation delivery device.

9. The method of claim 8 wherein the data parameter includes a combination of multiple single data parameters.

10. The method of claim 8 wherein the data parameter is fluence.

11. The method of claim 8 wherein the data parameter is linac output.

12. The method of claim 8 wherein the data parameter is leaf timing.

13. The method of claim 8 wherein the data parameter is jaw position.

14. The method of claim 8 wherein the data parameter is couch position.

15. The method of claim 8 wherein the data parameter is gantry position.

* * * * *